US009943078B2

(12) United States Patent
Kravitz et al.

(10) Patent No.: US 9,943,078 B2
(45) Date of Patent: Apr. 17, 2018

(54) ORGAN TRANSPORT APPARATUS WITH SAMPLE COMPARTMENTS

(71) Applicant: LIFELINE SCIENTIFIC, INC., Itasca, IL (US)

(72) Inventors: David Kravitz, Barrington Hills, IL (US); Christopher P. Steinman, Sandy, UT (US); David Pettinato, Schaumburg, IL (US); Matthew Copithorne, Farmingham, MA (US); Brian Otts, Warrior, AL (US); Robert J. Allen, Crystal Lake, IL (US); Frank P. Nanna, Algonquin, IL (US); Peter Demuylder, Londerzeel (BE)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 0 days.

(21) Appl. No.: 15/163,088

(22) Filed: May 24, 2016

(65) Prior Publication Data
US 2016/0338344 A1 Nov. 24, 2016

Related U.S. Application Data

(62) Division of application No. 13/545,210, filed on Jul. 10, 2012, now Pat. No. 9,402,389.

(51) Int. Cl.
*A01N 1/02* (2006.01)

(52) U.S. Cl.
CPC ......... *A01N 1/0252* (2013.01); *A01N 1/0247* (2013.01); *A01N 1/0273* (2013.01)

(58) Field of Classification Search
None
See application file for complete search history.

(56) References Cited

U.S. PATENT DOCUMENTS

| 4,502,295 A | 3/1985 | Toledo-Pereyra |
| 4,745,759 A | 5/1988 | Bauer et al. |

(Continued)

FOREIGN PATENT DOCUMENTS

| EP | 0 475 144 A2 | 3/1992 |
| EP | 1 688 124 A1 | 8/2006 |

(Continued)

OTHER PUBLICATIONS

Shepard, BM. Important Policy Notice, United Network for Organ Sharing, Dec. 9, 2010, pp. 1-67.*

(Continued)

*Primary Examiner* — Jill A Warden
*Assistant Examiner* — Benjamin R Whatley
(74) *Attorney, Agent, or Firm* — Oliff PLC

(57) ABSTRACT

An apparatus for at least one of storage, treatment, assessment and transport of an organ or tissue includes a cooling container configured to cool the organ or tissue, a perfusion circuit configured to perfuse the organ or tissue, and a sample compartment for holding a biological sample. Preferred apparatus has a first internal compartment under a first cover (lid) of the apparatus that includes the coolant container and the sample compartment. The apparatus can include a second internal compartment under a second cover (lid) of the apparatus, the second internal compartment including at least part of the perfusion circuit and a sample compartment.

12 Claims, 7 Drawing Sheets

(56) References Cited

U.S. PATENT DOCUMENTS

| | | | |
|---|---|---|---|
| 5,157,930 | A | 10/1992 | McGhee et al. |
| 5,285,657 | A | 2/1994 | Bacchi et al. |
| 5,356,771 | A | 10/1994 | O'Dell |
| 5,391,136 | A | 2/1995 | Makowka |
| 5,441,170 | A | 8/1995 | Bane, III |
| 5,586,438 | A | 12/1996 | Fahy |
| 6,354,104 | B1 * | 3/2002 | Feagin ............... A61B 10/0096 220/210 |
| 6,673,594 | B1 | 1/2004 | Owen et al. |
| 7,278,270 | B2 | 10/2007 | Culp et al. |
| 7,749,693 | B2 | 7/2010 | Brassil et al. |
| 2004/0050849 | A1 | 3/2004 | Pickles |
| 2006/0208881 | A1 | 9/2006 | Suzuki |
| 2007/0048725 | A1 | 3/2007 | Arrington |
| 2008/0169214 | A1 | 7/2008 | Genovesi |
| 2008/0219885 | A1 | 9/2008 | Horstman |
| 2010/0304352 | A1 | 12/2010 | Patrick, III et al. |
| 2011/0076666 | A1 | 3/2011 | Brassil |
| 2011/0129908 | A1 | 6/2011 | Owen et al. |
| 2011/0136096 | A1 | 6/2011 | Hassanein et al. |
| 2011/0173023 | A1 | 7/2011 | LeClair et al. |
| 2012/0276620 | A1 | 11/2012 | Kravitz et al. |
| 2013/0177897 | A1 | 7/2013 | Kravitz et al. |
| 2014/0220550 | A1 | 8/2014 | Van Der Plaats et al. |

FOREIGN PATENT DOCUMENTS

| | | | |
|---|---|---|---|
| EP | 1688124 A1 * | 8/2006 | ............... A01N 1/02 |
| EP | 2301337 A2 | 3/2011 | |
| WO | 03/030769 A2 | 4/2003 | |
| WO | 2004/089235 A2 | 10/2004 | |
| WO | 2009/041806 A1 | 4/2009 | |
| WO | 2012/125782 A2 | 9/2012 | |
| WO | 2012/148690 A1 | 11/2012 | |
| WO | 2013032319 A1 | 3/2013 | |
| WO | 2013/106248 A2 | 7/2013 | |

OTHER PUBLICATIONS

Specimens for Histocompatibility Testing (Guidelines for OPOs, Author: Unknown. The examiner was unable to verify publication date, but an email to the examiner from the UNOS publishers stated that this document was approved by OPTN/UNOS Board of Directors in Dec. 2006 and published on the web at some point in 2007.*

Oct. 17, 2016 Office Action issued in Chinese Patent Application No. 201380046643.3.

Nov. 30, 2015 Office action issued in Chinese Patent Application No. 201380046643.3.

Jun. 11, 2015 Office Action issued in U.S. Appl. No. 13/545,184.

World Health Organization (WHO), Manual on the management, maintenance and use of blood cold chain equipment, 2005, pp. 1-92, Published 2005. ISBN 9241546735.

Salvalaggio et al, "Crossmatch Testing in Kidney Transplantation: Patterns of Practice and Associations with Rejection and Graft Survival"; Saudi J Kidney Dis Transpl. Jul. 2009; 20(4): 577-589.

Demetris et al, "A clinicopathological Study of Human Liver Allograft Recipients Harboring Performed IgG Lymphocytotoxic Antibodies", Hepatology, Sep. 1992; 16(3); 671-681.

Singh et al, "Positive, Warm T cell crossmatch in cardiac transplantation: with transient vasculitis and without hyperacute rejection", Transplantation, May 1982; 33(5); 564-566.

Strobel, E., "Hemolytic Transfusion Reactions", Transfus Med Hemother; 2008; 35; pp. 346-353.

Dec. 22, 2014 Office Action issued in U.S. Appl. No. 13/545,184.

Barcode Sticker: http://www.google.com/url?sa=t&rct=j&q=&esrc=s&frm= 1 &sou ce=web&cd= 1 & ved=OCCMOFjAA&url=http%3A %2F%2 Fwww.usdtl.com%2F literature_961 08%2FTamper_ vident_requisition_form_barcode_sticker article &ei=FOJVPf5NqH IsOSx1ILoDw &usg=AFOjCNF700y09xxbaJ82rvmnvPWU93Srmw&bvm=bv. 81456516,d.cWc ; posted online Dec. 11, 2007.

Locking container loops: ttp://web.archive.org/web/2011 0524000451 /http://reusabletranspack.com/templates/insulated %20contai ners/PB09%20 POP%20%20Insulated%20Containers. html.

Patrick, Charles, "Waters Adsvanced Viability Evaluation System WAVES," Jun. 2009, pp. 1-12, IGL Group, USA.

Aug. 11, 2009 Picture of Waters WAVES device taken from a trade show in France.

Steinman et al, U.S. Appl. No. 13/545,184, filed Jul. 10, 12012.

Mar. 28, 2014 Written Opinion of the International Searching Authority issued in International Patent Application No. PCT/US2013/049580.

Mar. 28, 2014 International Search Report issued in International Patent Application No. PCT/US2013/049580.

Anonymous, "SaBTO: Guidance on the Microbiological Safety of Human Organs, Tissues and Cells Used in Transplantation," The Advisory Committee on the Safety of Blood, Tissues and Organs, Feb. 21, 2011, pp. 1-60.

Anonymous, "Guidance for Industry: Eligibility Determination for Donors of Human Cells, Tissues and Cellular and Tissue-Based Products (HCT/Ps)," U.S. Department of Health and Human Services, Aug. 1, 2007, pp. 1-70.

Anonymous, "LifePort Kidney Transporter Operator's Manual", Organ Recovery Systems, Jul. 21, 2007.

Feb. 14, 2014 International Search Report issued in International Patent Application No. PCT/US2013/049584.

Feb. 14, 2014 Written Opinion of the International Searching Authority issued in International Patent Application No. PCT/US2013/049584.

Oct. 31, 2017 Office Action Issued in U.S. Appl. No. 15/190,360.

Specimens for Histocompatibility Testing (Guidelines for OPOs, Author: Unknown. pp. 1-9. Approved at UNOS board meeting in Dec. 2006 and publically available Jan. 2007) (Year: 2007).

* cited by examiner

ORGAN TRANSPORT APPARATUS WITH SAMPLE COMPARTMENTS

CROSS REFERENCE TO RELATED APPLICATION

This application is a divisional application of U.S. application Ser. No. 13/545,210, filed Jul. 10, 2012, the contents of which are incorporated herein by reference.

BACKGROUND

Biological samples may be used for a variety of reasons in conjunction with an associated organ or tissue that is being stored, transported, assessed and/or treated in a perfusion apparatus. Typically, biological samples are transported at the same time as the organ or tissue but the samples and the organ or tissue are not cooled simultaneously at the same temperature within a single apparatus. Documents such as medical records relating to each of the biological samples and the organ or tissue are typically transported in separate devices.

The practice of storing or transporting organs or tissue, biological samples and documents associated with the organs or tissues may suffer certain shortfalls. When biological samples and documents relating to an organ or tissue are separately stored and/or transported from the organ or tissue, the likelihood that they may be misplaced, misassociated and/or damaged is increased. If documents for the organ or tissue are lost or cannot be correlated with the organ or tissue with certainty, then a doctor or clinician may refuse to transplant the organ or tissue to a recipient or otherwise use the organ or tissue. If the documents are lost or cannot be correlated to the organ or tissue or biological sample, results from any testing or use of the biological samples, organ or tissue may be invalid or disregarded.

The practice of storing or transporting biological samples with an organ or tissue also suffers certain deficiencies. Some biological samples need to be handled to maintain viability in a similar manner as an organ or tissue. For example, sterility and temperature requirements may be required for the organ or tissue and the biological samples. Thus, an efficient and more effective means of cooling a biological sample simultaneously with an organ or tissue is desired.

SUMMARY

A perfusion device for transport, assessment, treatment and/or storage of an organ or tissue as described herein may be configured to carry one or more biological samples in addition to the organ or tissue. Such a device may reduce cost, conserve space, provide convenience, and/or increase security to the organ or tissue and the biological sample(s). The device may conveniently carry various biological samples of various sizes with the organ or tissue. Documents for each of the biological sample(s) and the organ or tissue may stay together in the same device to ensure that they are readily accessible and continuously associated with one another, which may readily allow confirmation that the organ or tissue and the biological sample(s) are suitable for use such as transplantation and/or testing. The device may efficiently and compactly meet sterility, viability and temperature requirements for the organ or tissue as well as the biological sample(s).

Exemplary implementations according to this disclosure may include an apparatus for at least one of storage, assessment, treatment and transport of an organ or tissue. The apparatus includes a coolant container configured to cool and optionally support the organ or tissue, and a sample compartment for holding a biological sample separate from the organ or tissue, wherein the coolant container is configured to cool and optionally support the sample compartment. The coolant container may include a first cavity and a second cavity, wherein the first cavity is configured to cool and optionally support the organ or tissue, and the second cavity is configured to cool and optionally support the biological sample. The first cavity and the second cavity may be separate from each other. The second cavity may define at least a portion of the sample compartment and/or be located in a corner of the coolant container.

Exemplary implementations according to this disclosure include a first internal compartment under a first cover of the apparatus, the first internal compartment including the coolant container and the sample compartment. The apparatus may include a second internal compartment under a second cover that is configured to close the apparatus in cooperation with the first cover, wherein the sample compartment is not accessible when the first cover is closed and the second cover is open or closed. The second internal compartment may include a second sample compartment, a heat-generating device and/or at least part of a perfusion circuit. An interior wall of the first internal compartment may act in cooperation with the second cavity to define the sample compartment. The sample compartment may be located in a corner of the first internal compartment located farthest away from the second internal compartment.

Exemplary implementations according to this disclosure include a sample compartment that is configured to support a sample container (specimen cup). The sample compartment may be shaped to complementarily support the specimen cup. The apparatus may include the sample compartment being configured to support a first specimen cup with a first shape and the second sample compartment being configured to support a second specimen cup with a second shape, wherein the first and second shapes are different. The apparatus may include a cooling structure that provides external cooling air to cool the apparatus.

Exemplary implementations according to this disclosure include a kit in the form of a saleable package containing a sterilized basin configured to hold an organ or tissue in a perfusion apparatus, a sterilized cradle configured to support the organ or tissue in the sterilized basin, and a sterilized specimen container.

Exemplary implementations according to this disclosure include a method of storage, assessment, treatment and/or transport of an organ or tissue. The method includes transporting the organ or tissue in a basin supported in the coolant container, and transporting a biological sample, which is associated with the organ or tissue, in a specimen container placed in the sample compartment. The method may include cooling both the organ or tissue and the biological sample to a same temperature.

BRIEF DESCRIPTION OF THE DRAWINGS

Exemplary implementations are described herein with reference to the following figures wherein.

DETAILED DESCRIPTION OF EMBODIMENTS

The following exemplary embodiments refer to transport, storage, treatment and/or assessment apparatus for an organ or tissue and a biological sample. It should be appreciated that, although the exemplary embodiments according to this disclosure may be applicable to specific applications, the depictions and/or descriptions included in this disclosure are not intended to be limited to any specific application. Any perfusion apparatus and method that may advantageously involve an organ or tissue and a biological sample as described in an exemplary manner in this disclosure are contemplated.

Blood samples and tissue samples may be used in laboratory testing to conduct a variety of tests to obtain information about an organ or tissue, the donor and/or the recipient. For example, they may be used to identify specific antigens. An antigen is any substance that causes the immune system to produce antibodies against that substance. A tissue sample may be, for example, but not limited to, a tissue sample of a donor such as blood, lymph or a spleen. Tissue samples may be acquired during a biopsy to identify potential diseases in the organ or tissue prior to transplantation. Tissue samples may be used in laboratory testing for tissue typing. Tissue typing is a test that determines whether organ compatibility exists between the donor and a potential recipient of transplantation. Serology analyzes blood serum and other bodily fluid and may be conducted with blood and/or other tissue samples to determine allergic reactions in the organ or tissue recipient and diagnose and/or treat other potential concerns prior to transplantation or other use of an organ or tissue. These tests may also help in predicting or diagnosing medical problems immediately after transplantation. Thus, it may be advantageous to have tissue samples readily available prior to organ transplantation or other use for these testing purposes.

Figure 1:
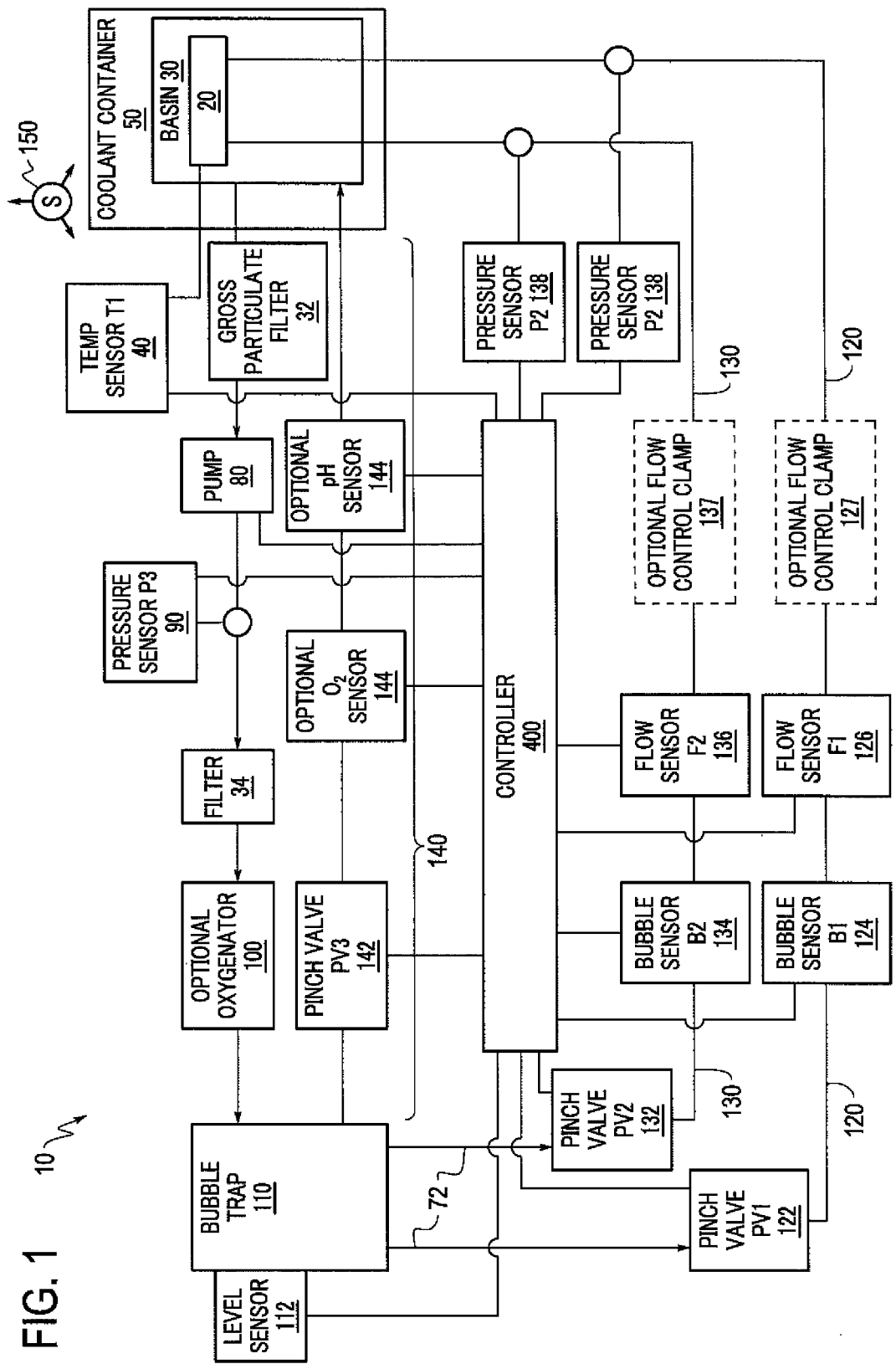
FIG. 1 illustrates a schematic diagram of an exemplary perfusion apparatus for an organ or tissue.
Figure 3:
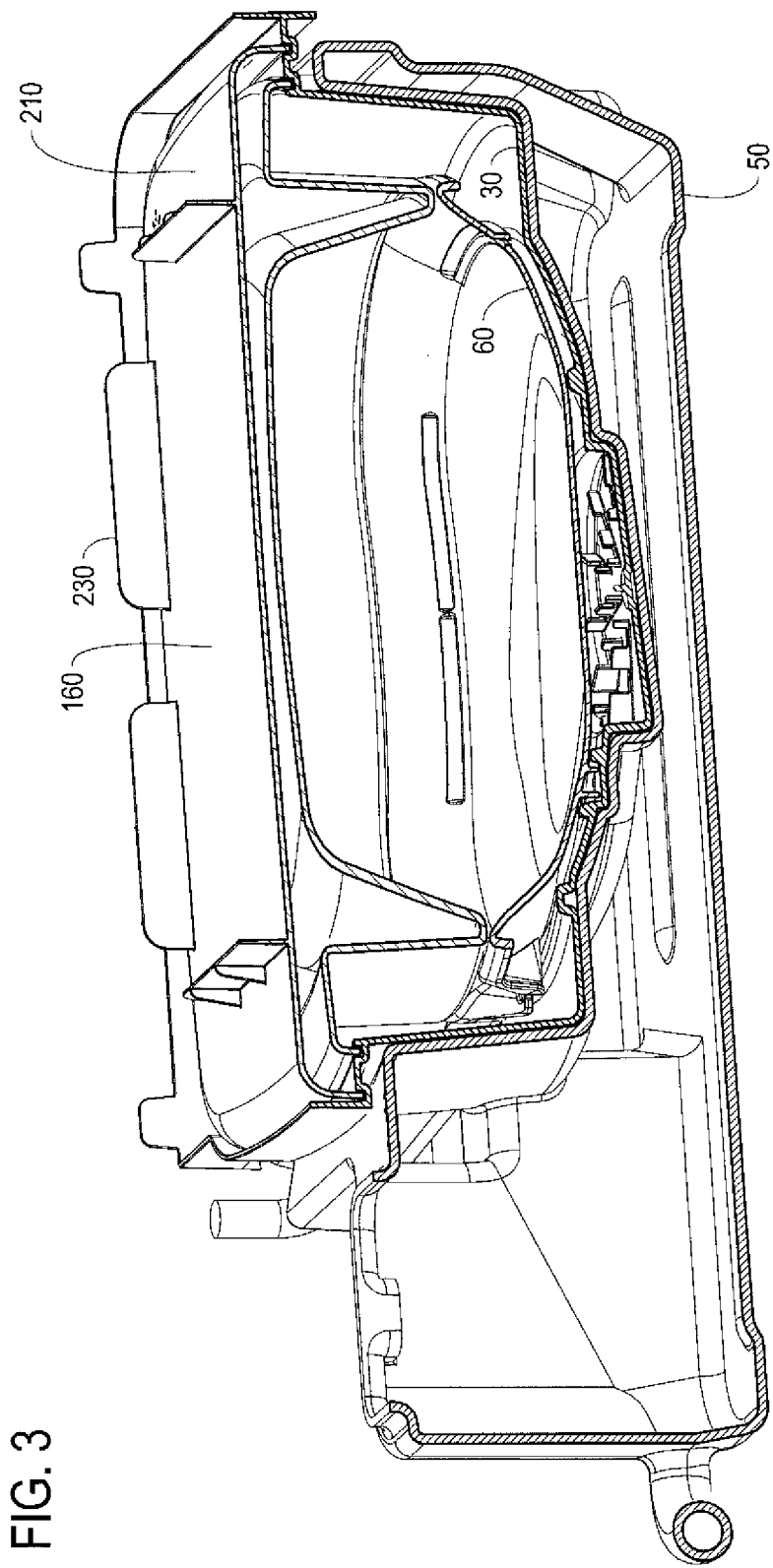
FIG. 3 illustrates a first exemplary cross-sectional perspective view, taken along the line 3-3 in FIG. 2, of an internal compartment of the apparatus.

FIG. 1 is a schematic diagram of a perfusion apparatus 10 for an organ 20. The organ 20 may preferably be a liver, kidney, heart, lung, or intestine, but may be any human or animal, natural or engineered, healthy, injured or diseased organ or tissue. As used herein, the term "organ" is used to mean organ and/or tissue unless otherwise specified. The apparatus includes a basin 30 in which the organ may be placed. The basin 30 may hold a cradle 60 as illustrated in FIG. 3, which preferably includes a surface on which the organ 20 is disposed when the organ 20 is in the apparatus 10. The basin 30 may include a first filter that can function as a gross particulate filter. The basin 30 and/or the cradle 60 are preferably configured to allow a perfusate bath to form around the organ 20. The basin 30 and/or apparatus 10 may also include one or more temperature sensors 40 located in or near the cradle 60. The apparatus 10 and/or basin 30 may include one or more additional temperature sensors 40, which may provide redundancy in the event of a failure and/or may provide temperature measurement at multiple locations. Preferably, the temperature sensor(s) 40 is an infrared temperature sensor. The temperature sensor(s) 40 is preferably disposed as close as practical to the organ 20 when the organ 20 is disposed in the cradle 60 in order to improve the usefulness and accuracy of the temperature sensor(s) 40, which preferably provide a temperature measurement of the perfusate that may be correlated to a temperature of the organ 20. Alternatively or additionally, the temperature sensor(s) 40 may be used to directly measure the temperature of the organ 20.

The basin 30 is preferably disposed within a recess of a coolant container 50 that may contain cold materials such as ice, ice water, brine or the like. Coolant container 50 may be permanently or removably attached to, or an integral, monolithic part of, apparatus 10. Thus, in use, the organ 20 is disposed within the cradle 60, which is disposed within the basin 30, which is disposed within a recess of the coolant container 50. Preferably, each of the basin 30, cradle 60 and coolant container 50 is configured, or keyed, to fit within its corresponding mating component in a single orientation in use. The configuration of the coolant container 50, basin 30 and cradle 60 may provide a configuration that provides cooling for the organ 20 without the contents of coolant container 50 contacting the organ 20 or the cradle 60. Although the coolant container 50 is described herein as containing ice, any suitable cooling medium can be used. Ice may be preferable due to the ease with which ice can be procured, but one of ordinary skill would understand that any suitable cooling medium, which could be an active cooling medium (such as a thermo electric cooler or a refrigerant loop) or a passive cooling medium similar to ice or ice water, or a combination thereof, may be utilized. The amount of ice, or other cooling medium, that can be placed within the coolant container 50 should be determined based upon the maximum time that cooling is to be provided while the organ 20 will be in the apparatus 10.

The cradle 60 may include components configured to securely restrain the organ 20 in place. Such components may, for example, include user selectable netting that is fastened to the cradle 60.

After passing through the filter 32, the perfusate flows along a first flow path 70 that includes a suitable fluid conduit 72, such as flexible or rigid tubing, a pump 80, a pressure sensor 90, a second filter 34, an optional oxygenator 100 and a bubble trap 110, each of which is discussed below.

The first filter 32 is preferably a relatively coarse filter (relative to the second filter 34). Such a coarse filter may be provided to prevent large particles, which may for example be byproducts of the organ or of the organ being removed from the donor, from entering and clogging fluid paths of the apparatus 10. The first filter 32 may be an integral part of the basin 30 or the first filter may be disposed elsewhere in the first flow path 70 downstream of the basin 30. The first filter 32 may also be a separate component from the basin 30 or disposed within the fluid conduit 72.

The first flow path 70 may also include a pump 80. The pump 80 may be any pump that is suitable in connection with perfusing of organs. Examples of suitable pumps may include hand-operated pumps, centrifugal pumps and roller pumps. If a roller pump is included, the roller pump may include a single channel or flow path (where only one tube is compressed by the rollers) or the roller pump may include multiple, parallel channels or flow paths (where multiple tubes are compressed by the rollers). If multiple, parallel channels or flow paths are included, the rollers may preferably be disposed out of phase or offset so that pulses created by the rollers are out of phase, which may result in a fluid flow out of the roller pump that is relatively less pulsatile than would be the case with a single roller. Such a multiple channel roller pump may achieve a constant flow rate or a minimally pulsatile flow rate, which may be advantageous depending on the other components in the flow path and/or the type of organ being perfused.

The flow path 70 may include a pressure sensor 90. The pressure sensor 90 may be preferably disposed after the outlet of the pump 80 in order to monitor and/or be used to control the pressure produced at the outlet of the pump by way of a suitable controller. The pressure sensor 90 may provide continuous or periodic monitoring of pressure.

The flow path 70 may include an oxygenator 100 such as an oxygenator membrane or body to provide oxygenation to the perfusate. Oxygen may be provided to the oxygenator 100 by any suitable means. Suitable oxygen sources may include pure oxygen or mixed gases such as air. The gas may be compressed, such as in a high-pressure cylinder, liquefied as would be stored in a dewar, or drawn from the surrounding atmosphere. Preferably, the oxygen may be provided by way of an oxygen generator, which may be separate from the apparatus 10 or integral to the apparatus 10. Oxygen may be generated through any suitable means, some examples of which include through pressure swing adsorption using a molecular sieve, through a ceramic oxygen generator (a solid state oxygen pump) or through decomposition of water.

The flow path 70 may include a bubble trap 110. The bubble trap 110 preferably separates gas bubbles that may be entrained in the perfusate flow and prevents such bubbles from continuing downstream and entering the organ 20. The bubble trap 110 may also function as an accumulator that reduces or eliminates pulsatility of the perfusate flow. The bubble trap 110 may include a volume of gas, initially or through the accumulation of bubbles, such that pressure fluctuations in the perfusate are dampened or eliminated.

The bubble trap 110 may include a vent that allows purging of gas during start up or a purging process. The vent may be connected to or part of purge flow path 140. The vent is preferably open during a start up process so that any air or other gas may be purged from the perfusate path 70. When the vent is open, valves 122, 132 will preferably both be closed. Once the gas is purged from the perfusate path 70, the vent may preferably be closed. The vent may be closed manually or may be closed automatically by way of a suitable controller.

The bubble trap 110 may include a level sensor 112. A level sensor 112 may optionally be used during the purging process to determine when the purging is complete and/or may be used to determine when the purging process needs to be repeated, which may happen after gas has been trapped in the bubble trap 110. Also, through use of the level sensor 112 and the vent, the accumulator function of the bubble trap can be tuned to account for differing amplitudes and frequencies of pulsatility in the perfusate flow. The accumulator function of the bubble trap may be tuned, for example, by adjusting the volumetric ratio of air to perfusate fluid.

The bubble trap 110 may have any number of outlets, as needed for a given application of the perfusion apparatus 10. In FIG. 1, three outlets are shown connected to three different flow paths, which may be particularly suited for the perfusion of a liver. When perfusing a liver, the three paths preferably include portal flow path 120 connected to the portal vein of a liver, hepatic flow path 130 connected to the hepatic artery of a liver, and bypass flow path 140 that provides a return path to the basin 30. There may also be a port in any fluid path that allows fluid access to the perfusate solution. The port may preferably be located in the bubble trap 110. This port may preferably include a luer type fitting such that a user may extract a small a sample of the perfusate for analysis. The port may also be utilized by a user to add substances such as drugs to the perfusate without opening the basin.

As shown in FIG. 1, the portal flow path 120 and hepatic flow path 130 may optionally include similar or different components such as valves 122, 132; bubble sensors 124, 134; flow sensors 126, 136; flow control clamps 127, 137; and pressure sensors 128, 138. Each similar component may function in a similar manner, and such pairs of components may optionally be structurally and/or functionally identical to reduce manufacturing costs. Flow sensors 126, 136 may preferably be ultrasonic sensors disposed around tubing, although any suitable sensor may be used. Ultrasonic sensors may be advantageous because in normal usage such sensors do not come into contact with the perfusate and therefore are not in the sterile path. Such an implementation of ultrasonic sensors does not require replacement and/or cleaning after use.

Valves 122, 132 may be pinch valves that function to squeeze tubing and reduce or shut off flow, but any suitable valve may be used. Pinch valves may be advantageous because in normal usage they do not come into contact with the perfusate and therefore do not require replacement and/or cleaning after use.

Preferably, the bubble sensors 124, 134 are ultrasonic sensors disposed around tubing, although any suitable sensor may be used. Similar to pinch valves, ultrasonic sensors may be advantageous because in normal usage they do not come into contact with the perfusate and therefore do not require replacement and/or cleaning after use. Instead, ultrasonic sensors can be disposed in contact with, adjacent to or around an external surface of tubing in order to sense bubbles.

Flow control clamps 127, 137 may be used to fine-tune the flow rate in one or both of portal flow path 120 and hepatic flow path 130. Preferably, the organ provides self-regulation to control flow that exits the bubble trap 110 and is divided between the portal flow path 120 and the hepatic flow path 130. In such self-regulated flow, pressure sensors 128, 138 provide overpressure monitoring. In the event that pressure delivered to the organ in either or both of the portal flow path 120 or the hepatic flow path 130 exceeds a predetermined threshold, the apparatus 10 can automatically stop and/or reduce the flow rate provided by the pump 80 to prevent damage to the organ. In addition or alternatively, the pressure sensors 128, 138 may be used to generate warning signals to the user and/or to an appropriate controller as pressures approach the predetermined threshold. An alternate software algorithm may be employed to allow the apparatus 10 to perfuse at a preferred pressure. For example, a software algorithm may allow a doctor or clinician to select a specific pressure and vary the flow rate accordingly.

After exiting one or both of the portal flow path 120 and hepatic flow path 130, perfusate flows through the organ and returns to the basin 30 to form an organ bath.

Bypass flow path 140 may include a valve 142, and/or sensors such as oxygen sensor 144 and pH sensor 146. Preferably, the valve 142 is a pinch valve and may be of similar configuration to valves 122 and 132, but any suitable valve may be used. The oxygen sensor 144 and the pH sensor 146 may be used to determine the state of the perfusate. Preferably, the bypass flow path 140 is only used during a purging or priming process, although it may also be used during perfusion, preferably continuously, to monitor perfusate properties in real time.

The organ perfusion apparatus 10 may also include an accelerometer 150. Preferably the accelerometer 150 is a three-axis accelerometer, although multiple single axis accelerometers may be used to the same effect. The accelerometer 150 may be used to continuously or periodically monitor and/or record the state of the apparatus 10. Monitoring may include monitoring for excessive shocks as well as attitude of the apparatus 10. For example, if a pitch or a roll exceeds a pre-set alarm limit, the action of the pump 80 may be momentarily interrupted to stop the flow of perfusate until that specific condition is corrected. By implementing such monitoring, misuse or potentially inappropriate conditions of the apparatus 10 can be detected and recorded and appropriate action can be taken.

Preferably, all components of the apparatus 10 that come into contact with perfusate and/or an organ and/or a biological sample are disposable and/or easily replaced. Such disposable items may be included in a kit or saleable package. For example, such a kit may include packaging such as plastic or shrink wrap packaging containing some or all of the components that come into contact with an organ, biological sample, and/or perfusate. In embodiments, the tubing, filter, oxygenator and bubble trap may be packaged together in a manner preconfigured to be placed into the apparatus 10. The cradle and basin may be packaged individually or together, and optionally together with the tubing, filter, oxygenator and bubble trap, and specimen cups may be packaged with or separate from such other components.

Specimen cup(s) 170D, basin 30, cradle 60 and other components may be included in a disposable kit and may be sterilized prior to use. For example, the specimen cup(s) 170D may be wrapped in a separate bag having a closed environment to maintain sterility prior to storing a biological sample and placing the specimen cup(s) 170D in the apparatus 10. In this manner, contamination to the tissue or organ and biological samples can be minimized. The specimen cup(s) 170D may be a disposable item, optionally packaged in a sterile kit with other disposable components of the perfusion apparatus 10 such as the basin, and/or cradle, and/or other components, and discarded after use.

The apparatus 10 may include storage compartments for items other than the organ 20. For example, the apparatus 10 may include a document compartment 160 (FIG. 3) to store documents and/or charts related to the organ 20. Also, the apparatus 10 may include one or more sample compartment(s) 170(A-C). The sample compartment(s) 170(A-C) may be configured, for example, to store liquid and/or solid tissue samples. The sample compartment(s) 170(A-C) may be advantageously disposed near, or separated from, the coolant container 50 to provide cooling that may be the same, similar to, or different from the cooling provided for the organ 20.

Figure 2:
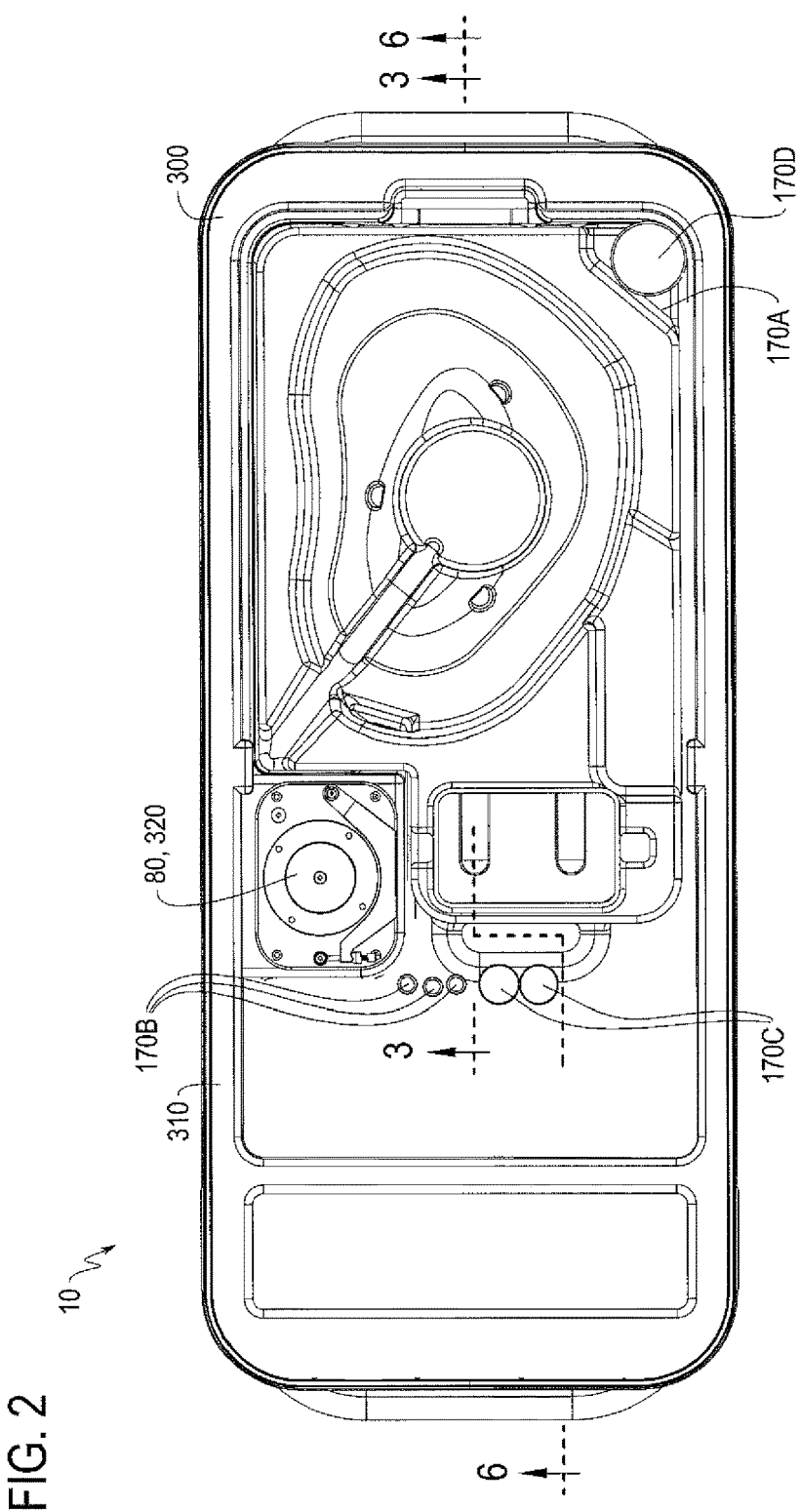
FIG. 2 illustrates a top view of an exemplary perfusion apparatus in an uncovered state.

FIG. 2 illustrates a top view of an exemplary apparatus 10 when the cover 200 and second cover 220 are removed. A plurality of sample compartment(s) 170(A-C) may be advantageously disposed at various locations in the apparatus 10. The sample compartment(s) 170(A-C) may carry different types of biological samples (not shown), which may include, but are not limited to, vasculature and blood samples.

A container such as a sealable specimen cup 170D may be placed within the sample compartment(s) 170(A-C) to advantageously accompany the organ 20 during perfusion, transport, and/or storage of the organ 20. The sample compartment(s) 170(A-C) may be configured to secure and support various sizes and shapes of the specimen cup. For example, the specimen cups 170D may include, but are not limited to, blood tubes, plastic tissue sample containers and plastic urinalysis cups. The specimen cups 170D may vary in size. Different biological samples such as blood, tissues and organ vasculature may be carried by various types of specimen cups 170D. For example, blood tubes are generally between 5-10 cm.sup.3 in size. A standard urinalysis cup is a type of specimen cup 170D that may be used to carry liver blood vessels. Conical tubes are commonly used for spleen and lymph nodes. They are generally between 5-20 cm.sup.3 in size.

The specimen cup(s) may preferably be used to hold biological samples such as donor vasculature. Donor vasculature may be used to rebuild vasculature, such as a vein or an artery, cooperating with the organ 20 in the body of the recipient during organ transplantation. Rebuilding of vasculature may be necessary in situations where the vasculature of the organ recipient may be damaged and/or not functional before, during or after organ transplantation. It may be advantageous to carry donor vasculature with the organ 20 for co-storage and/or transport of vasculature or other biological specimens. Carrying donor vasculature with the organ 20 may provide the advantage of facilitating rebuilding the vasculature of the organ recipient with the donor vasculature so that the compatibility of the vasculature to the organ 20 may be maintained. By maintaining the compatibility of the vasculature to the organ 20, the likelihood that the recipient's body may reject the donor organ 20 may be minimized. Additionally, proper functionality of the organ 20 within the recipient's body may be improved.

Figure 4:
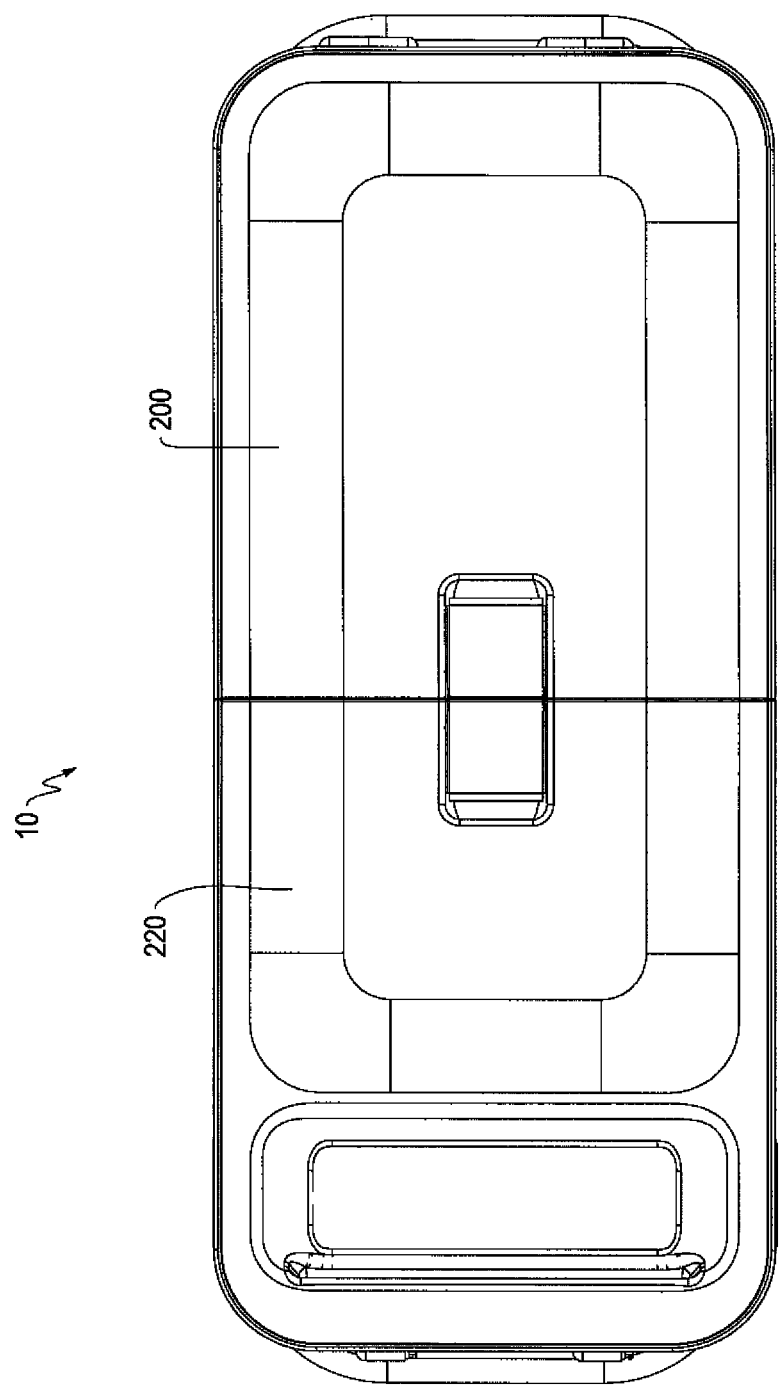
FIG. 4 illustrates an exemplary top view of the apparatus of FIG. 2 in a covered state.

Sample compartment(s) 170(A-C) may be located in internal compartments 300, 310 of the apparatus 10. A compartment, for example the first internal compartment 300, may be a section of the apparatus 10 that is defined by a plurality of walls or regions that divide the apparatus 10. A compartment may be structurally divided within the apparatus 10 or functionally divided by the relative location of components of the apparatus 10. Compartments may be defined as specific enclosures for a group of elements that function in relation to one another. Compartments may also be defined with respect to the position of corresponding covers. For example, FIG. 4 illustrates that components under these covers may be defined as being in different compartments. First internal compartment 300 may be defined to be under cover (lid) 200 and a second internal compartment 310 may be defined to be under the second cover (lid) 220. The first internal compartment 300 may include the basin 30, part or all of the coolant container 50 and/or the cradle 60. The second internal compartment 310 may include the pump 80, the bubble trap 110, the second filter 34, valves 122, 132, bubble sensors 124, 134 and/or flow sensors 126, 136.

As can be particularly appreciated from FIG. 1, an overall container for organ perfusion apparatus 10 may hold numerous components in a small volume. Thus, volume for biological samples and/or documents is preferably reserved and allocated in specific, efficient ways in embodiments described herein.

Preferably, a specimen cup 170D may be located in a sample compartment 170(A), the first sample compartment, adjacent to where the cradle 60 and organ 20 may be placed. It may be advantageous to place the specimen cup 170D carrying donor vasculature, for example, near the organ 20 if the organ 20 and donor vasculature require low temperatures for preservation. Thus, it may be helpful to place biological samples having similar viability requirements as the organ 20 near the organ 20. On the other hand, biological samples such as blood, for example, may not require such low temperatures and therefore may not need the same level of temperature control. Accordingly, sample containers such as blood tubes, for example, may be located at other positions in the apparatus away from the organ 20.

The coolant container 50 may have one or more cavities or recesses in which the specimen cup 170D and/or basin 30 may be placed. The basin 30 and the specimen cup 170D may be placed in the same cavity or in separate cavities of the coolant container 50. Bottom and sides of the basin 30 and/or the specimen cup 170D may be completely enclosed by the cavity. Alternatively, the basin 30 and/or the specimen cup 170D may be at least partially enclosed by the cavity. For example, a portion of a side surface of the specimen cup 170D may not be surrounded by the cavity of the coolant container 50. The coolant container 50 may have a plurality of sample compartments 170A to support multiple specimen cups 170D depending on the size and shape of the organ/ tissue receiving cavity.

Figure 5:
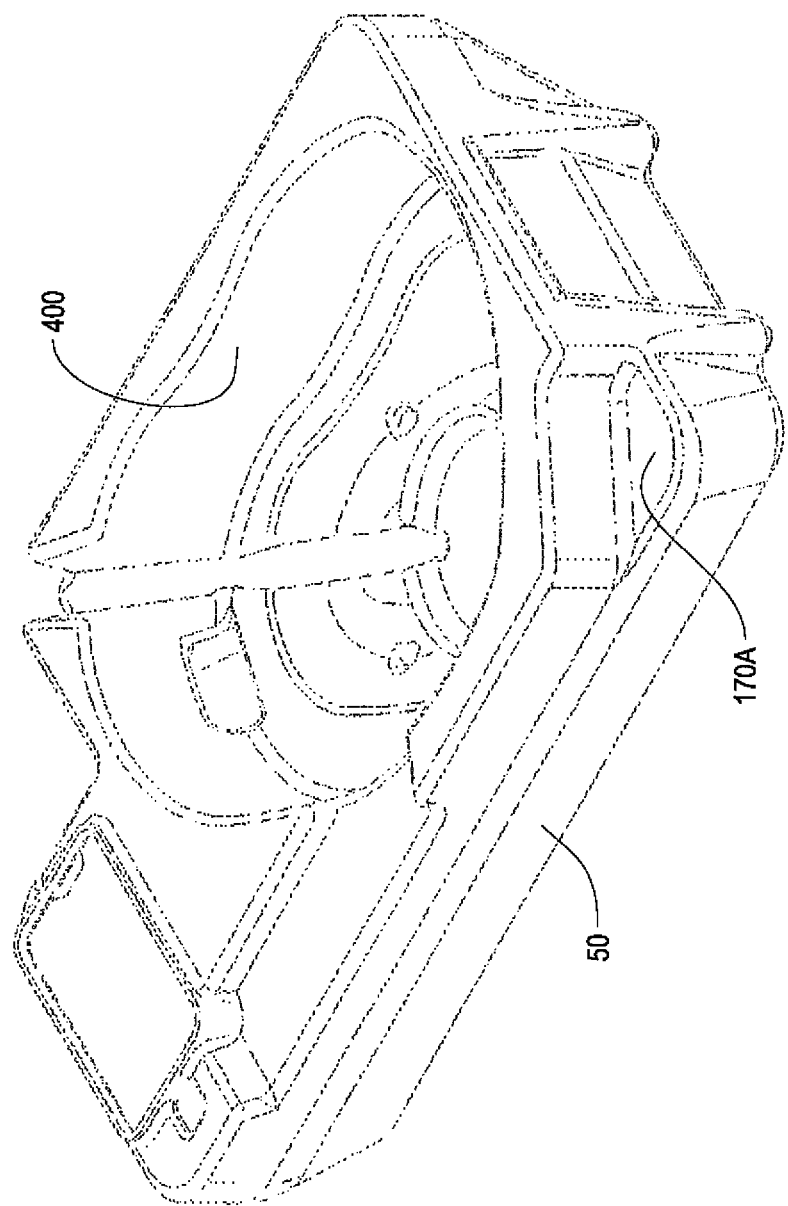
FIG. 5 illustrates an exemplary perspective view of the coolant container of FIG. 2.

FIG. 5 illustrates a coolant container 50 with a first cavity 400 where the basin 30 may be placed and a cavity defining sample compartment 170A where one or more specimen cup 170D may be placed. The walls of the first cavity 400 may surround the basin 30 on its bottom and sides. For example, the first cavity 400 may have a bottom wall that supports the basin 30. The specimen cup 170D may be partially surrounded by walls of the coolant container 50 in the sample compartment 170A, as illustrated in FIGS. 2 and 5. The walls of the sample compartment 170A may include a sidewall and a bottom wall. Preferably, the sidewall of the sample compartment 170A may be located at a corner of the coolant container 50. Internal walls of the first internal compartment 300 in combination with the walls of the coolant container 50 may provide support for and/or restrain the specimen cup 170D in the apparatus 10. Alternatively, multiple sidewalls of sample compartment 170A may be defined by surfaces of the coolant container 50. The amount of surface area of the coolant container 50 may be selected to achieve a desired temperature range for the biological sample(s).

It may be advantageous to place basin 30 and specimen cup 170D in cavities in the coolant container 50 so that the organ 20 and the biological sample are cooled in a similar manner. Placing the basin 30 and the specimen cup 170D in separate cavities of the coolant container 50 may provide a similar degree of cooling to the organ 20 and the biological sample. Additionally, having separate cavities in the coolant container 50 allows the specimen cup 170D to be positioned apart from the organ 20, basin 30 and/or cradle 60 so that the specimen cup 170D does not act as an obstacle or contamination source during the handling of the organ 20, basin 30 and/or cradle 60 in the apparatus 10. It may also be advantageous for the specimen cup 170D and basin 30 to be in thermal contact with multiple surfaces of the coolant container 50 to maximize cooling efficiency. The amount of thermal contact between the coolant container 50 and the specimen cup 170D and/or basin 30 may be optimized to achieve a desired temperature range.

The first internal compartment 300 may include a cavity to support the coolant container 50 and/or the specimen cup(s) 170D. The cavity of the first internal compartment 300 may be at various positions in the apparatus 10 depending on the size and shape of the organ 20, basin 30 and/or cradle 60. For example, the first internal compartment 300 may have a cavity in which basin 30, most of coolant container 50, and/or cradle 60 are located, as illustrated in FIG. 2. The walls of the first internal compartment 300 may be configured to surround at least a portion of a side of specimen cup 170D. Preferably, the basin 30 and specimen cup 170D may be positioned to be in contact with walls of the coolant container 50 and/or walls of the first internal compartment 300 so that temperatures established by the cooling medium can be more effectively regulated. This configuration advantageously allows for separate temperature regulation of the basin 30 and the specimen cup 170D. Energy from heat-generating components of the second internal compartment 310 may be used to control the temperature of the biological samples in specimen cups 170D via at least heat transfer from the second internal compartment 310. On the other hand, the temperature of the organ 20 in the basin 30 may be more isolated and directly controlled by the coolant container 50. Various configurations of the cradle 60, basin 30, sample compartment(s) 170(A-C) and coolant container 50 may be contemplated to achieve the desired temperature regulation.

FIGS. 2 and 5 illustrate that a sample compartment 170A may be positioned in a corner of the first internal compartment 300 that is relatively far from the second internal compartment 310. The position of the sample compartment 170A may be dependent upon the shape and size of the coolant container 50 and/or basin 30 to maintain a compact configuration in the first internal compartment 300 and/or apparatus 10. Preferably, the sample compartment 170A may be located at a position distant from the second internal compartment 310, and may be defined at least in part by an internal surface of the first internal compartment 300 that is physically separated from the second internal compartment 310. For example, the cradle 60 and/or basin 30 may be located between the sample compartment 170A and the second internal compartment 310. Most of the heat and/or vibration generated during the operation of the apparatus 10 is produced by components in the second internal compartment 310. Thus, it may be advantageous to locate the sample compartment 170A as far away as practical from the second internal compartment 310 to more effectively and more efficiently maintain the temperature of the specimen cup 170D in the sample compartment 170A and to provide a more stable environment. Alternatively, it may be advantageous to locate sample compartment(s) 170A at various positions in the first internal compartment 300 depending on the desired temperature. For example, a specimen cup 170D may be positioned closer to the second internal compartment 310 where heat generating components are located if a higher temperature is desired for a biological sample. Thus, placement of the sample compartment(s) 170A can take advantage of heating and/or cooling throughout the apparatus 10. Multiple sample compartments 170A may be contemplated at various locations in the first internal compartment 300.

As discussed above, the coolant container 50 may contain a cooling medium (such as ice, ice water or brine, not shown) used to cool the organ 20. If a sample compartment 170(A-C) is disposed near the coolant container 50, the coolant container 50 may also advantageously cool the sample compartment 170(A-C) and thus the contents of a specimen cup 170D. The sample compartment(s) 170A may be located at least partially within a cavity of the coolant container 50 and/or in contact with the coolant container 50 to cool the contents of the coolant compartment(s) 170A with the same cooling medium as the organ 20. This configuration may regulate the temperature of a biological sample in specimen cup 170D and the organ 20 such that these temperatures are as close as practical. The coolant container 50 may at least partially surround the basin 30 and/or the sample compartment(s) 170A. It may be advantageous not to surround a portion of the basin 30 and/or sample compartment 170A, for example, for ease of handling and access.

A portion of the coolant container 50 may extend into the second internal compartment 310, or within the area under the second cover 220. This portion may include an opening that allows the coolant container 50 to be filled with the cooling medium. The opening of this portion of the coolant container 50 may include a cap with a locking mechanism and/or a sealing mechanism to ensure that the cooling medium is fully enclosed within the coolant container 50 and to provide a leak free arrangement. This configuration advantageously allows the cooling medium to be added or changed without opening the cover 200 of the first internal compartment 300.

Preferably, the cooling medium may maintain a temperature between 1.degree. C. and 15.degree. C. in the sample compartment(s) 170A and the basin 30. More preferably, the cooling medium may maintain a temperature between 5.degree. C. and 10.degree. C. in the sample compartment(s) 170A and the basin 30. For example, the cooling medium may maintain a temperature between 6.degree. C. and 8.degree. C. in the sample compartment 170A and the basin 30. Preferably, the temperature may be maintained for a period of time greater than 25 hours. More preferably, the temperature may be maintained for a period of time greater than 30 hours. For example, the temperature may be maintained between 6.degree. C. and 8.degree. C. for a period of time greater than 35 hours at standard temperature and pressure (STP). Positioning the coolant container 50 with the cooling medium, the basin 30 and/or the sample compartment(s) 170(A-C) in relationship with one another provides the advantage of cooling the biological sample and the organ 20 simultaneously and efficiently by the same cooling system. This may be especially helpful for certain biological samples where requirements such as viability, temperature and compatibility are present. Additionally, the biological samples and the organ 20 may be monitored and examined in the same proximate area of the apparatus 10.

Figure 6:
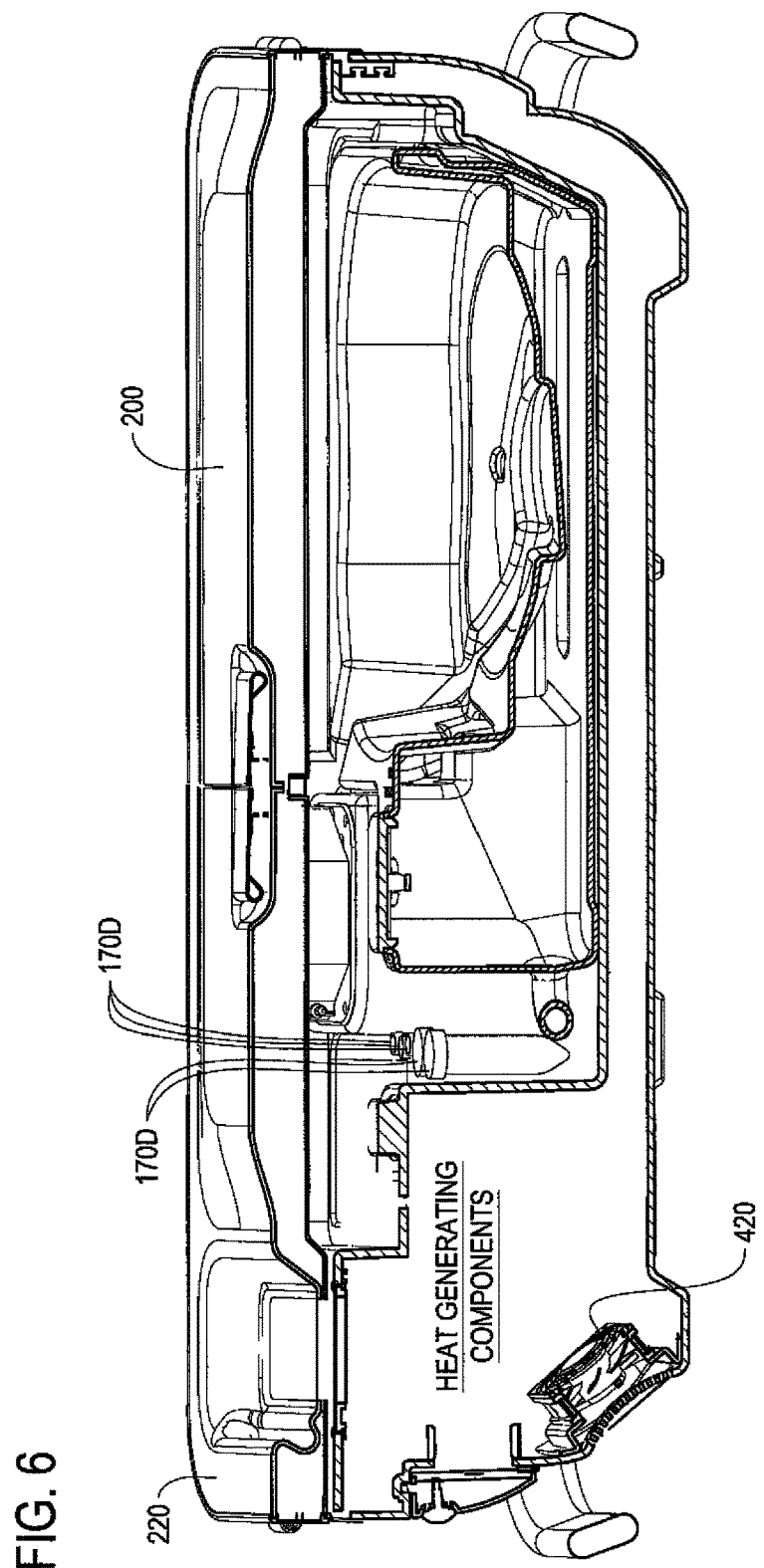
FIG. 6 illustrates a second exemplary cross-sectional perspective view, taken along the line 6-6 in FIG. 2, of the apparatus.
Figure 7:
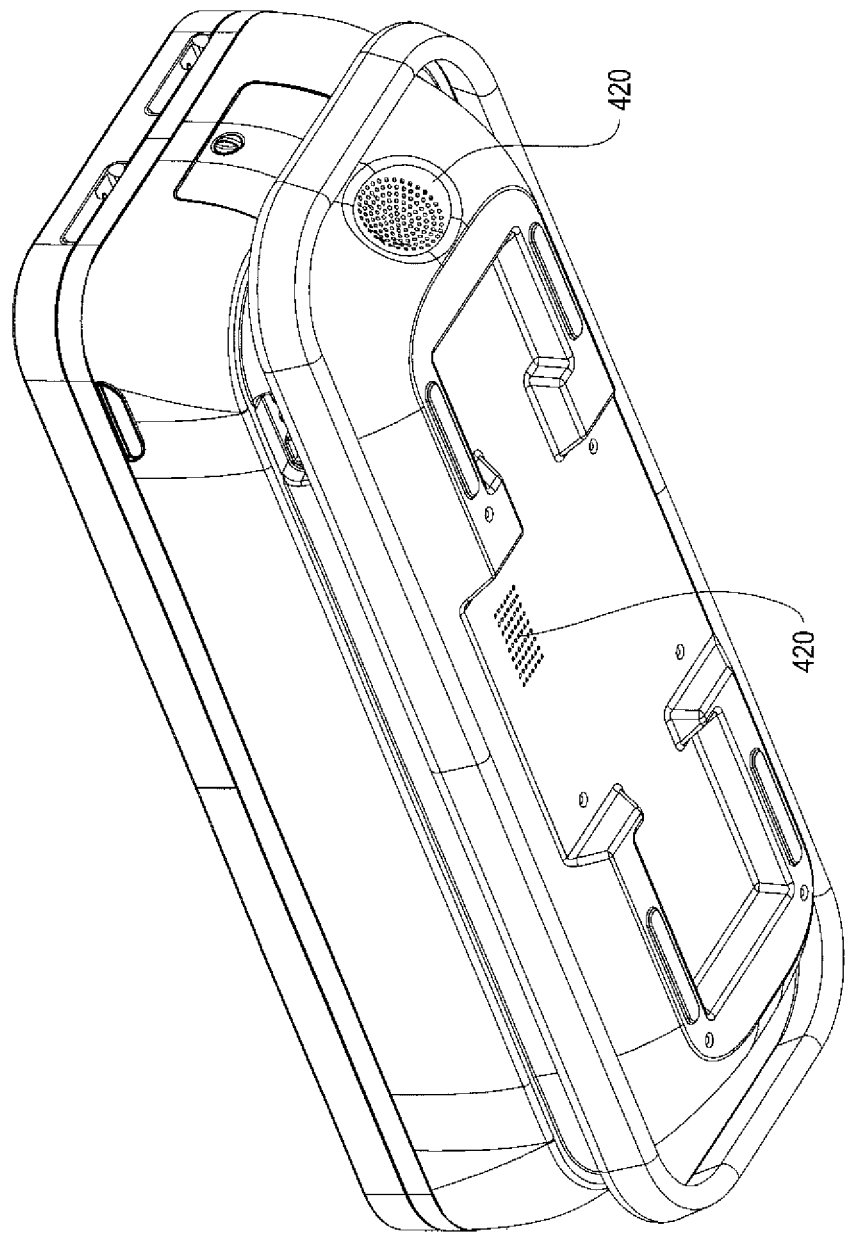
FIG. 7 illustrates an exemplary bottom perspective view of the apparatus of FIG. 2.

The apparatus 10 may include a motor 320 for the pump 80. The apparatus 10 may include a cooling structure 420 that is configured to provide external cooling air to cool the motor 320 and draw away heat from the interior of the apparatus 10, as illustrated in FIGS. 6 and 7. The cooling structure 420 may include a fan that is configured to draw outside air into the apparatus 10 and exhaust internal air from the apparatus 10. FIG. 7 illustrates that the cooling structure may include inlet and outlet vents to cycle air into and/or out of the apparatus 10. It may be advantageous to position the fan and/or the vents at high temperature areas of the apparatus 10 to efficiently remove unwanted heat. Components of the apparatus 10 that produce heat may define the locations of the high temperature areas. These components of the apparatus 10 may include, but are not limited to, the motor, power supply and transformer, batteries, pump 80, a display screen and other electronics. Vents may be positioned at various locations of the apparatus 10 to prevent overheating of components, maximize airflow throughout the apparatus 10, and achieve temperature regulation of various sample compartment(s) 170(A-C). External cooling air may advantageously provide improved thermal efficiency of the apparatus 10 during operation of the motor.

A plurality of biological samples may also or alternatively be carried in sample compartments 170B and/or 170C. Specimen cups may be placed within separate sample compartments 170B and/or 170C of the apparatus 10 to accompany the organ 20 during perfusion, transport, treatment and/or storage of the organ 20. The sample compartments 170B and/or 170C may be located in the second internal compartment 310 of the apparatus 10. Preferably, the sample compartments 170B and/or 170C may be located in the second internal compartment 310 of the apparatus 10 where heat generating components may be located. For example, sample compartments 170E and/or 170C may be located adjacent to the pump 80 and may also be located adjacent to each other. Preferably, sample compartments 170B and/or 170C are used with biological samples that require less strict temperature control and/or warmer temperatures than provided for the basin 30 and sample compartment(s) 170A.

The sample compartments 170B, 170C may be positioned at various locations depending on the locations of the components of the perfusion circuit 330 to optimize space constraints, to take advantage of the flow of air in the apparatus 10, to achieve the desired temperature range for each of the biological samples, and/or to maintain a compact configuration.

The combination of at least the cooling structure 420, the position of the coolant container 50, the location of the heat generating components, the position of open spaces around the respective heat generating components, and the flow path where the air in the apparatus 10 flows may minimize the effects of heat produced by the heat generating components and aid in maintaining an appropriate temperature level for the sample compartments 170B, 170C. Although these sample compartments are not located in the first internal compartment 300, the temperature of biological samples in them can be effectively regulated in the second internal compartment 310.

The sample compartments 170B and/or 170C may be cooled by the cooling medium in the coolant container 50, as illustrated in FIG. 2, even though they are not bounded by the coolant container 50. This configuration may be advantageous because some biological samples may have less stringent temperature or viability requirements, or may require warmer temperatures, than other biological samples. As a result, space optimization and compactness of the apparatus 10 is achieved while providing temperature regulation of the sample compartments 170B and/or 170C. Various types of biological samples may be advantageously placed relatively distant from the organ 20 and/or coolant container 50, yet within the apparatus 10, to satisfy space constraints and convenience while maintaining security and/or cooling requirements of the organ 20 and/or biological samples.

The location of sample compartments 170B, 170C under the second cover 220 in the second internal compartment 310, as illustrated in FIG. 4, allows the biological samples to be accessed only from the interior of the apparatus 10. Moreover, the biological samples may be accessible without opening the cover 200 of the first internal compartment 300 where the organ 20 may be located. This configuration may advantageously protect the organ 20 from unauthorized access, minimize cooling disruptions, and/or maintain the sterile environment. Additionally, having two separate internal compartments 300, 310 and two respective covers 200, 220 may provide more effective temperature regulation of the organ 20 and biological samples within the apparatus 10.

Preferably, the sample compartment(s) 170(A-C) may be configured to act as holders to secure and support the specimen cup(s) 170D. Close fitted sample compartments may hold the specimen cup(s) 170D. The sample compartments 170A, 170B and/or 170C may be of the same or different shapes. Thus, the sample compartments 170(A-C) in the apparatus 10 may carry various shapes and sizes of biological samples. The sample compartments 170(A-C) of the apparatus 10 need not be constructed for specific shapes and sizes. Handling fixtures, for example, may accompany the specimen cups) to secure them in the sample compartments 170(A-C) of the apparatus 10. Such handling fixtures may also be provided in a kit with specimen cup(s) and/or other components. This configuration may advantageously provide a versatile apparatus 10 to carry biological samples of various shapes and sizes. The specimen cup(s) 170D may be for single use and therefore disposable. The sample compartments 170(A-C) may be configured to secure and support different sizes and shapes of specimen cup(s) 170D. The sample compartments 170(A-C) may be insulated to protect the specimen cups) 170D from damage. Insulation may also protect the specimen cup(s) 170D during turbulent transport of the apparatus 10.

It may be advantageous that documents are safely stored and kept together with an organ. If the documents for the organ are lost or disassociated with the organ, then a doctor or clinician may refuse to transplant the organ and/or otherwise use the organ. This is because the transplantation or other use may require data to ensure, for example, compatibility of the organ to a recipient, chain of custody to ensure that the organ has not been tampered with during transport, identity of the organ to confirm that the organ is the organ requested for transplant or other use, and/or viability of the organ to ensure that the organ is stable and prepared for transplantation or other use. If documents for the biological samples are lost or cannot be correlated to the organ and samples being transplanted, the results from any testing of the biological samples may not be used or useful because the original state of the biological samples and their relationship to the organ is uncertain.

The apparatus 10 may carry associated documents, such as donor medical records and/or organ data, in the document compartment 160. The document compartment 160 may be positioned between the cover 200 and lid 210 in the first internal compartment 300, or in the second internal compartment 310. Preferably, the cover 200 and the lid 210 form the document compartment 160. FIG. 3 illustrates a portion of the document compartment 160 formed on the lid 210. Wall portions 230 may protrude from a top surface of the lid 210. The wall portions 230 may be integral to the lid 210 or they may be separate parts that are connected to the lid 210 during assembly. The wall portions 230 may act as side surfaces of the document compartment 160 and the top surface of the lid 210 may form the bottom internal surface of the document compartment 160. When the first internal compartment cover 200 closes the first internal compartment 300, the document compartment 160 may be closed. As a result, the bottom surface of the first cover 200 may be the top internal surface of the document compartment 160 and the top surface of the lid 210 may be the bottom internal surface of the document compartment 160. Alternatively, or in addition, lids of the compartment 310 may have such a structure.

It should be appreciated that various features disclosed above and other features and functions, or alternatives thereof, may be desirably combined into many other devices. Also, various alternatives, modifications, variations or improvements therein may be subsequently made by those skilled in the art, which are also intended to be encompassed by this disclosure.

The invention claimed is:

1. An apparatus for at least one of storage, treatment, assessment and transport of an organ or tissue, the apparatus comprising:
    a first internal compartment including a coolant container and a first sample compartment that has a bottom and is enclosed by one or more sidewalls,
        the coolant container including therein a cooling medium and having a cooling surface configured to cool the organ or tissue, and
        the first sample compartment being separate from the cooling medium and being configured to hold a biological sample container separate from the organ or tissue;
    a document compartment configured to store documents separate from the organ or tissue; and
    a first cover configured to move relative to the document compartment and disposed such that the first internal compartment and the document compartment are under the first cover so that the first cover covers the document compartment when closed,
    wherein the document compartment is located between the first cover and a lid of the first internal compartment.

2. The apparatus of claim 1, further comprising a second internal compartment and a second cover such that the second internal compartment is disposed under the second cover.

3. The apparatus of claim 2, wherein the second internal compartment includes at least one heat-generating device and a second sample compartment, the second sample compartment being configured to hold a biological sample separate from the organ or tissue.

4. The apparatus of claim 2, wherein the first sample compartment is not accessible when the first cover is closed regardless of whether the second cover is open or closed.

5. The apparatus of claim 3, wherein the second sample compartment is not accessible when the second cover is closed regardless of whether the first cover is open or closed.

6. The apparatus of claim 3, wherein the first internal compartment includes a third sample compartment, the third sample compartment being located closer to the heat-generating device than the first sample compartment.

7. The apparatus of claim 3, wherein the heat-generating device is a pump.

8. The apparatus of claim 3, wherein the second internal compartment further includes a cooling structure that cools the second internal compartment.

9. The apparatus of claim 1, wherein the coolant container includes a cavity such that a wall of the cavity also forms one of the sidewalls of the first sample compartment.

10. The apparatus of claim 9, wherein the cavity of the coolant container is configured to receive a basin for holding the organ or tissue.

11. The apparatus of claim 1, wherein the document compartment includes wall portions that are perpendicular to the first cover.

12. A method of using the apparatus of claim 1, the method comprising:
    transporting an organ or tissue in a basin in contact with the cooling surface; and
    simultaneously transporting a biological sample, which is associated with the organ or tissue, in a specimen container in the first sample compartment.

* * * * *